US00PP10305P

United States Patent [19]

Kientzler

[11] Patent Number: Plant 10,305

[45] Date of Patent: Mar. 24, 1998

[54] NEW GUINEA IMPATIENS PLANT NAMED 'XANTHIA'

[75] Inventor: Ludwig Kientzler, Gensingen, Germany

[73] Assignee: Paul Ecke Ranch, Inc., Encinitas, Calif.

[21] Appl. No.: 780,411

[22] Filed: Jan. 9, 1997

[51] Int. Cl.[6] ..... A01H 5/00

[52] U.S. Cl. ..... Plt./87.6

[58] Field of Search ..... Plt./87.6

*Primary Examiner*—James R. Feyrer
*Attorney, Agent, or Firm*—C. A. Whealy

[57] ABSTRACT

A new and distinct cultivar of New Guinea Impatiens plant named 'Xanthia', characterized by its large bright orange-colored flowers; mounded and compact growth habit; freely branching plant habit; and dark green, glossy, non-variegated foliage.

1 Drawing Sheet

The present invention relates to a new and distinct cultivar of New Guinea Impatiens plant, botanically known as *Impatiens hawkeri*, known by the name 'Kixant', and hereinafter referred to by the cultivar name 'Xanthia'.

The new cultivar is a product of a planned breeding program conducted by the inventor in Gensingen, Germany. The objective of the breeding program was to develop new varieties that have a uniform plant habit, attractive flower colors, good flower form and numerous flowers per plant.

The new cultivar originated from a cross made by the inventor of a proprietary seedling selection identified as O452 as the male, or pollen parent, with the proprietary seedling selection identified as O67 as the female, or seed patent. The cultivar 'Xanthia' was discovered and selected by the inventor as a flowering plant within the progeny of the stated cross in a controlled environment in Gensingen, Germany. Asexual reproduction of the new cultivar by terminal cuttings taken at Gensingen, Germany, has shown that the unique features of this new Impatiens are stable and reproduced true to type in successive generations of asexual reproduction.

The following traits have been repeatedly observed and are determined to be the unique characteristics of 'Xanthia'. These characteristics in combination distinguish 'Xanthia' as a new and distinct cultivar:

1. Large bright orange-colored flowers.
2. Mounded and compact growth habit.
3. Freely branching.
4. Dark green, glossy, non-variegated foliage.

The new New Guinea Impatiens is similar in flower color to the New Guinea Impatiens cultivar 'Orange' (U.S. plant pat. applied for). However in side-by-side comparisons in Encinitas, Calif., under commercial practice, plants of the new New Guinea Impatiens differed from plants of the cultivar 'Orange' in the following characteristics:

1. Plants of the new New Guinea Impatiens more compact than plants of the cultivar 'Orange'.
2. Leaves of plants of the new New Guinea Impatiens are smaller but glossier than leaves of plants of the cultivar 'Orange'.
3. Flowers of plants of the new New Guinea Impatiens are larger and more rounded than flowers of plants of the cultivar 'Orange'.
4. Peduncles of plants of the new New Guinea Impatiens are shorter and redder than flower spurs of plants of the cultivar 'Orange'.

A detailed comparison of plants of the new New Guinea Impatiens and the cultivar 'Orange' appears in Chart A at the end of the specification.

The accompanying colored photographs illustrate the overall appearance of the new cultivar, showing the colors as true as it is reasonably possible to obtain in colored reproductions of this type.

The first photograph comprises a top perspective view of a typical plant of 'Xanthia'.

The second photograph comprises a close-up view of typical flowers and upper (left) and lower (right) surfaces of leaves of the cultivars 'Orange' (top of photo) and 'Xanthia' (bottom of photo).

Flower and foliage colors in the photographs may differ from the actual colors due to light reflectance.

The cultivar 'Xanthia' has not been observed under all possible environmental conditions. The phenotype may vary somewhat with variations in environment such as temperature and light intensity, without, however, any variance in genotype. The following observations, measurements and comparisons describe plants grown 10-cm pots in Encinitas, Calif., under commercial practice in a fiberglass-covered greenhouse with day temperatures ranging from 23 to 29C and night temperatures ranging from 16 to 18C and about 3,000 footcandles.

In the following description, color references are made to The Royal Horticultural Society Colour Chart except where general terms of ordinary dictionary significance are used.

Classification:

*Botanical.*—*Impatiens hawkeri 'Xanthia'*.

*Commerical.*—New Guinea Impatiens cv. 'Xanthia'.

Parentage:

*Male parent.*—Proprietary seedling selection O452.

*Female parent.*—Proprietary seedling selection O67.

Propagation:

*type cutting.*—Terminal cuttings.

*Time to initiate roots.*—About 15 days with 21C soil temperature.

Plant description:

*Plant form.*—Mounded and compact.

*Growth habit.*—Low vigor. Freely branching, dense and bushy. Suitable for 10 to 25-cm containers.

*Plant size.*—Height: About 18 cm. Width or spread: About 18 cm.

*Lateral branches.*—Quantity: Seven to ten. Size: Length: About 8 cm. Diameter: About 1 cm. Internode length: 3 to 4 cm. Color 146A with stripes of 60B.

*Foliage description.*—Leaves simple, generally symmetrical, abundant, opposite or in whorls of three, horizontal to plant and flat in aspect. Size, largest leaves: Length: About 12 cm. Width: 3.5 to 4 cm. Shape: Ovate with acuminate apex, attenuate base and ciliate margin. Texture: Smooth, glossy. Color: Young foliage, upper surface: Greener than 146A. Young foliage, lower surface: 147C. Fully expanded foliage, upper surface: 147A. Fully expanded foliage, lower surface: 147C. Venation, upper surface: 58C. Venation, lower surface: 59A. Petiole: Size: Length: 4 to 4.5 cm. Diameter: About 4 mm. Color: 182A.

Flower description:

*Flower type and habit.*—Large bright orange-colored flowers. Freely and continuously flowering. Flowers arise from leaf axils. Usually eight flowers per lateral branch. Flowers positioned at or just above the foliage and face upward or outward. Flowers flat to slightly cupped and rounded rectangular. Flowers persistent.

*Flowering season.*—Year-round under greenhouse conditions. In the garden, flowering is continuous from spring until fall.

*Flower size.*—Length: About 7 cm. Width: About 65 cm. Depth: About 5 mm.

*Flower buds.*—Size Length: About 2.7 cm. Diameter: About 1.4 cm. Shape: Ovoid. Color: Top: 45A. Bottom: Brighter than 40A.

*Petals.*—Quantity: Five. Size (largest petals): Length: Top petal: About 3 cm. Middle petals: About 4 cm. Bottom petals: About 4.5 cm. Width: Top petal: About 5 cm. Middle petals: About 3.5 cm. Bottom petals: About 5 cm. Shape: Cordate with emarginate apex, cuneate or obtuse base and entire margin. Texture: Satiny, smooth. Color: When opening, upper surface: Iridescent, brighter than 40A. When opening, lower surface Iridescent, 40C. Fully opened, upper surface: Iridescent, brighter than 40A. Fully opened, lower surface: Iridescent, 40D. Fading to: Color does not fade.

*Spur.*—Length: 5 to 5.5 cm. Shape: Narrow and curved. Color: 59A.

*Peduncles.*—Length: About 5 cm. Angle: Upright. Strength: Strong. Color: 59A.

*Reproductive organs.*—Androecium: Stamen number: Five, anthers fused, filaments free. Anther shape: Obovate. Anther size: 7 by 4 mm. Anther color: Cream. Amount of pollen: Moderate. Pollen color: Cream. Gynoecium: Five-loculate fused. Gynoecium color: 144A.

Disease resistance: Under commercial conditions, resistance nor susceptibility to pathogens has not been observed.

Seed development: Seed production is not usually observed.

CHART A

| CHARACTERISTIC | 'XANTHIA' | 'ORANGE' |
|---|---|---|
| GROWTH HABIT | Mounded and compact | Upright and mounded |
| PLANT HEIGHT | About 18 cm | About 22 cm |
| PLANT WIDTH | About 18 cm | About 22 cm |
| LATERAL BRANCH LENGTH | About 8 cm | 11 to 12 cm |
| LATERAL BRANCH DIAMETER | About 1 cm | About 1.2 cm |
| INTERNODE LENGTH | 3 to 4 cm | 6 to 7 cm |
| STEM COLOR | 146A with stripes of 60B | 148A with stripes of 59B |
| LEAF LENGTH | About 12 cm | 14 to 16 cm |
| LEAF WIDTH | 3.5 to 4 cm | About 5.5 cm |
| LEAF TEXTURE | Smooth, glossy | Smooth, somewhat glossy |
| LEAF COLOR, YOUNG, UPPER SURFACE | Greener than 146A | Greener than 137A |
| LEAF COLOR, YOUNG, LOWER SURFACE | 147C | 138B |
| LEAF COLOR, MATURE, UPPER SURFACE | 147A | Greener than 147A |
| LEAF COLOR, MATURE, LOWER SURFACE | 147C | 147B |
| LEAF VENATION COLOR, UPPER SURFACE | 58C | 59D |
| LEAF VENATION COLOR, LOWER SURFACE | 59A | 59B |
| PETIOLE LENGTH | 4 to 4.5 cm | About 5 cm |
| PETIOLE DIAMETER | About 4 mm | About 5 mm |
| PETIOLE COLOR | 182A | 185B |
| FLOWER SHAPE | Rounded triangular | Star-shaped |
| FLOWER LENGTH | About 7 cm | About 6.5 cm |
| FLOWER WIDTH | About 6.5 cm | About 6.2 cm |
| PETAL COLOR, WHEN OPENING, UPPER SURFACE | Brighter than 40A | Brighter than 40A |
| PETAL COLOR, WHEN OPENING, LOWER SURFACE | 40C | 40B |
| PETAL COLOR, OPENED, UPPER SURFACE | Brighter than 40A | Brighter than 40A |
| PETAL COLOR, OPENED, LOWER SURFACE | 40D | 40D |
| PETAL COLOR FADING TO | 40A | 40B |
| SPUR LENGTH | 5 to 5.5 cm | About 7 cm |
| PEDUNCLE LENGTH | About 5 cm | 5.5 to 6 cm |
| PEDUNCLE COLOR | 59A | 144B with stripes of 59A |
| FLOWER BUD COLOR | 40A/45A | 40A/43A |

It is claimed:

1. A new and distinct cultivar of New Guinea Impatiens plant named 'Xanthia', as illustrated and described.

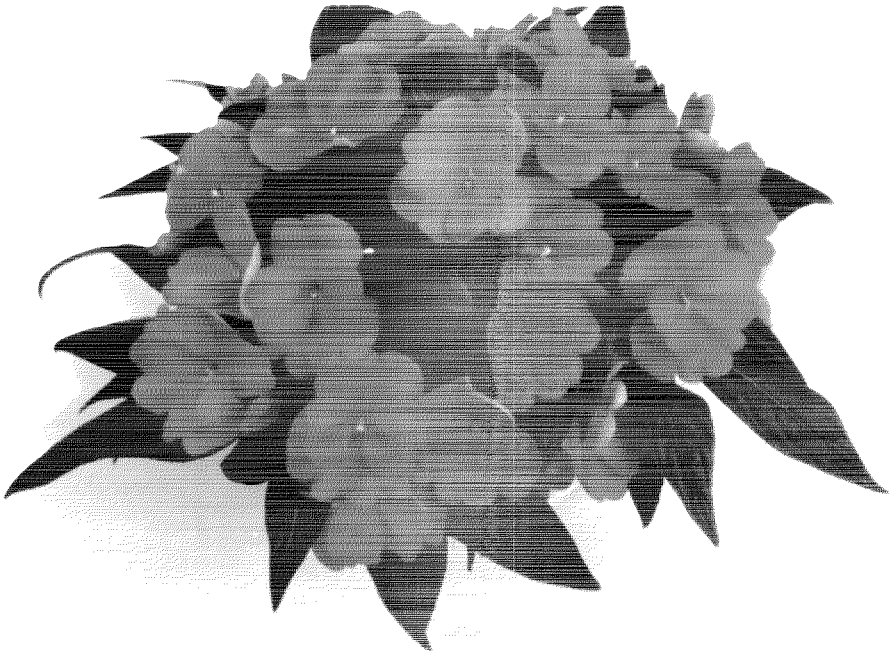
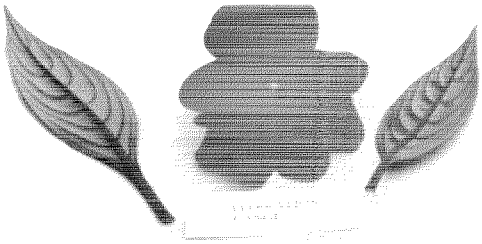
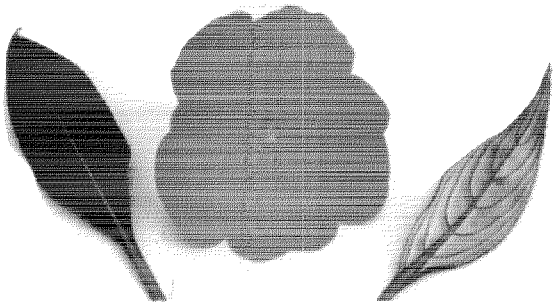

* * * * *